Figure 1A:
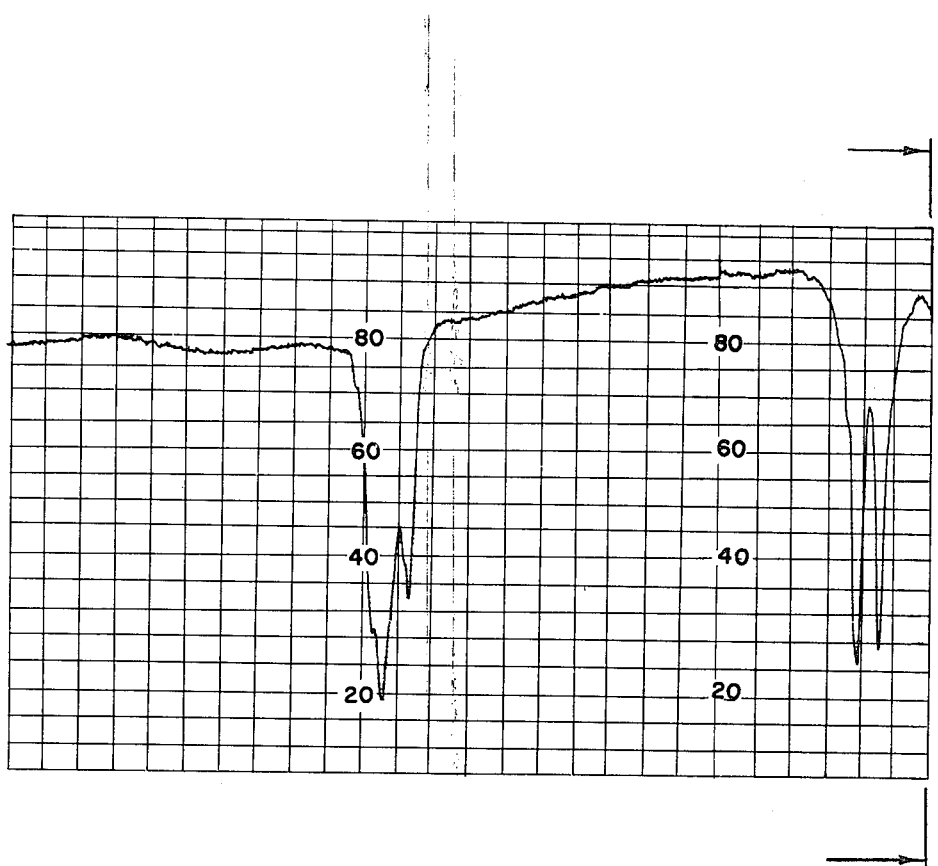

United States Patent [19]

Vandoni

[11] 4,277,489

[45] Jul. 7, 1981

[54] 1(P-CHLOROBENZOYL)-5-METHOXY-2-METHYL INDOLE-3-ACETIC ACID-3-OXO-ISOBENZOFURANYL ESTER AND PHARMACEUTICAL USE THEREOF

[75] Inventor: Guido Vandoni, Milan, Italy

[73] Assignee: Resfar S.r.l., Milan, Italy

[21] Appl. No.: 119,332

[22] Filed: Feb. 7, 1980

[30] Foreign Application Priority Data

Feb. 21, 1979 [IT] Italy .............................. 20398 A/79

[51] Int. Cl.³ .................... A61K 31/40; C07D 209/26
[52] U.S. Cl. ........................... 424/274; 260/326.13 A
[58] Field of Search ............ 260/326.13 A, 326.13 H, 260/343 BR; 424/274; 326/13 H

[56] References Cited

U.S. PATENT DOCUMENTS 3,103,515  9/1963  Zaugg et al. ...................... 260/343.3

FOREIGN PATENT DOCUMENTS 2740853  3/1979  Fed. Rep. of Germany ... 260/326.13 A

*Primary Examiner*—Anton H. Sutto
*Assistant Examiner*—D. B. Springer
*Attorney, Agent, or Firm*—Ladas & Parry

[57] ABSTRACT

This invention relates to a derivative of 1-(p-chlorobenzoyl)-5-methoxy-2-methyl indole-3-acetic acid with 3-oxo-1-isobenzofuranyl, linked by an ester bond, more particularly to 1-(p-chlorobenzoyl)-5-methoxy-2-methyl indole-3-acet-3-oxo-1-isobenzofuranyl ester, as well as to its preparation and therapeutical use as an analgesic and anti-inflammatory agent.

Said compound is prepared by reacting equi-molecular amounts of 1-(p-chlorobenzoyl)-5-methoxy-2-methyl indole-3-acetic acid and bromophthalide a few hours at room temperature, under a mild stirring, in the presence of a base.

3 Claims, 5 Drawing Figures

1(P-CHLOROBENZOYL)-5-METHOXY-2-METHYL INDOLE-3-ACETIC ACID-3-OXO-ISOBENZOFURANYL ESTER AND PHARMACEUTICAL USE THEREOF

DESCRIPTION OF THE INVENTION

The object of the present invention is a derivative of 1-(p-chlorobenzoyl)-5-methoxy-2-methylindole-3-acetic acid with 3-oxo-1-isobenzofuranyl, linked by an ester bond, its preparation and its therapeutic use as an analgesic and anti-inflammatory agent.

More precisely, the object of the present invention is 1-(p-chlorobenzoyl)-5-methoxy-2-methylindole-3-acet-3-oxo-1-isobenzofuranyl-ester, also called 1-(p-chlorobenzoyl)-5-methoxy-2-methyl indole -3-acetic acid 3-oxo-1-isobenzofuranyl ester.

The derivative according to this invention has the following empirical formula:

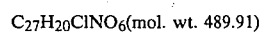

$C_{27}H_{20}ClNO_6$ (mol. wt. 489.91)

and corresponds to the following structural formula:

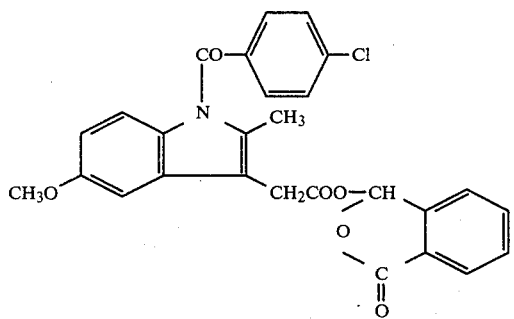

According to this invention, said compound is prepared by reacting equimolecular amounts of 1-(p-chlorobenzoyl)-5-methoxy-2-methylindole-3-acetic acid with bromophthalide a few hours at room temperature, under a mild stirring, in the presence of a base.

It is known that 1-(p-chlorobenzoyl)-5-methoxy-2-methylindole-3-acetic acid has a remarkable therapeutical activity, for example as an analgesic and anti-inflammatory agent, as well as some antipyretic action, whereby it is used in man, for example, for therapy of either rheumatic arthritis or other diseases against motory apparatus with a phlogistic component.

It is a feature of this acid, however, to exhibit some drawbacks connected, amongst other things, to the water-insolubility, the comparative acidity and a not negligible toxicity thereof.

Thus, the chemical-pharmacological investigation has been aiming for several years at characterising novel derivatives which, beside a potentiated therapeutical activity, explicate minor side effects.

For example, to the acidity level of 1-(p-chlorobenzoyl)-5-methoxy-2-methylindole-3-acetic acid, the gastro damaging and entero-damaging action is connected, which action is not fully overcome by making the pharmaceutical formulations protected by gastro-protecting excipients; in that event, indeed, even if the active substance gets through the gastric seat, dissolving and being absorbed in the intestinal seat, it may cause, even upon middle term treatments, lesions of enteric mucous membrane quite more serious than the gastric ones, since they often have a sly and silent course.

It has now been found that the compound which is an object of the present invention, exhibits a toxic component lesser than the one of the free acid, which in some cases, and particularly in the tender age subjects or in the aged persons, may give rise also to an increase of serum transaminase and to hepatopathic symptoms, detectable by the most common biochemical laboratory tests. In order to demonstrate the activity of the novel derivative which is an object of the present invention, some experimental tests have been performed against the known product, i.e. 1-(p-chlorobenzoyl)-5-methoxy-2-methylindole-3-acetic acid.

Firstly, the acute and subacute toxicity in the mouse orally has been tested.

For convenience, the products are so designed hereinafter:

Product A: 1-(p-chlorobenzoyl)-5-methoxy-2-methylindole-3-acetic acid or comparison product.

Product B: 1-(p-chlorobenzoyl)-5-methoxy-2-methylindole-3-acet-3-oxo-1-isobenzylfuranyl ester Table 1- Acute toxicity, in the mouse, of 1-(p-chlorobenzoyl)5-methoxy-2-methylindole-3-acetic acid (Product A) and of 1-(p-chlorobenzoyl) -5-methoxy-2-methylindole-3-acet-3-oxo-1-isobenzofuranyl ester derivative (Product B)

| Animals | Drug | Dose mg/kg | Mortality at 10th day % | LD$_{50}$ mg/kg Confidential limit |
|---|---|---|---|---|
| 10 | A | 10 | 40 | 15.4656 |
| 10 | A | 18 | 70 |  |
| 10 | A | 20 | 90 | 11.8409 |
| 10 | A | 25 | 100 |  |
| 10 | A | 28 | 100 | 9.0657 |
| 10 | B | 10 | 20 | 26.519 |
| 10 | B | 18 | 40 |  |
| 10 | B | 20 | 50 | 20.0887 |
| 10 | B | 25 | 60 |  |
| 10 | B | 28 | 70 | 15.2101 |

The symptomatology noticed at the sublethal doses has been of neurodepressing type.

The animal death, which occured within the first 24 hours would appear to be connected to cardiorespiratory arrest upon depression of the bulbar centers.

At the autopsical examination there was found a very marked gastroenteric hyperemia with presence of numerous ulcers as regards Product A, whereas, for Product B, object of the present invention, only a slight gastroenteric hyperemia, but no ulcer, was detected.

The maximum mortality was detected within the first 72 hours from administration.

In order to complete the picture of the possible ulcerogen activity, in the rat, of the product which is the object of this invention, a further research on the rat as against Product A, was performed.

Both the test molecules were suspended in 5% arabic gum and taken to solution.

The pharmacological treatment at the standard dose of 5 mg/kg was effected orally by means of a gastro-oesophageal probe.

The groups of animals were treated after 9, 24, 31, 50, 53, 56, 60 and 70 hours from beginning of the fasting. During the fasting period the animals received subcutaneously, 2 ml/die/animal of a 5% glucose solution in 9% NaCl. The animals were sacrificed, by decapitation, at 48 and 72 hours from beginning of the fasting; there were drawn for autopsic examination, jejunum and large intestine, which were examined microscopically in order to detect the presence of any possible ulcerations.

Results

Sacrificing at 48 hours from beginning of the fasting (3 administrations):

Product A —5 mg/kg:
Stomach diffusely hyperemic.
Small intestine (jejunum) slightly hyperemic, with presence of microulcers.
Large intestine (caecum) highly hyperemic.

Product B —5 mg/kg:
No pathological element to be shown at gastric level nor at intestinal level.

Sacrificing at 72 hours from beginning of the fasting (8 administrations)

Product A —5 mg/kg:
Stomach highly hyperemic with presence of evident macroulcers.
Jejunum diffusely hyperemic.
Caecum with hemorrhagic microareas.

Product B —5 mg/kg:
No considerable alteration at stomach level.
None at caecum level.
Jejunum slightly hyperemic.

At 72nd hour the liver of the animals treated with Product B was also examined macroscopically and microscopically, and nothing pathological resulted as regards the parenchyma or the cellular level.

In order to show the therapeutical activity of the derivative, which is an object of this invention, a research was carried out firstly on the anti-phlogistic activity as compared with the one of Product A.

The research was carried out in the rat by using the test of paw-oedema, induced by means of sub-plantar injection of carrageenin in a 1% solution. 0.1 ml of this solution was injected to each animal.

One hour before inoculation of the oedemigenous agent, the two test drugs were administered orally (gastric probe) to the different groups, according to the experimental scheme, and contemporaneously were measured, with a base value, the volume of the right untreated paw.

The treatment was effected on lots of five male animals of average weight of 240-270 g., according to the following experimental scheme:

1—three lots of control animals: 10 ml/kg mucilage of arabic gum;
2—one lot of animals treated with Product A—5 mg/kg;
3—one lot of animals treated with Product A—5.3 mg/kg;
4—one lot of animals treated with Product A—7 mg/kg;
5—one lot of animals treated with Product B—5 mg/kg;
6—one lot of animals treated with Product B—5.3 mg/kg;
7—one lot of animals treated with Product B—7 mg/kg.

At a distance of half an hour, one hour, two hours, three hours, four hours from inoculation of the phlogogenous agent, the volume increase of the right paw of the control animals as well as of the treated ones was measured by plethysmograph; from the results obtained it was noticed that the derivative which is an object of the present invention is signficantly more active, doses being equal, than the comparison product (Product A) within the first three hours.

Thus, it can be inferred that the anti-phlogistic effect of 1-(p-chlorobenzoyl)-5-methoxy-2-methylindole-3-acet-3-oxo-1-isobenzofuranyl ester is remarkably more precocious, as well as more marked, that the comparison product. As a second research on the therapeutical activity and practical utility of the derivative, which is an object of this invention, the antalgic activity in the mouse by means of the tail-compression test (Bianchi C. test—Brit. J. Pharmacol. 11, 104, 1956) was studied. The time elapsing between the algic stimulus and the reaction of the mouse trying to get out of said stimulus was determined in seconds.

The measure was effected at the times 0, 1, 2, 3 hours from administation of the derivative object of the present invention (Product B) and from administration of the comparison compound (Product A).

The test was effected on mice of 22 g. average weight, which had been divided into lots of six animals each, before and after the oral treatment performed according to the following scheme:

1—two lots of control animals: 0.5 ml/animal of mucilage of 5% arabic gum;
2—one lot treated with Product A—4 mg/kg;
3—one lot treated with Product A—7 mg/kg;
4—one lot treated with Product B—4 mg/kg;
5—one lot treated with Product B—7 mg/kg.

From the results obtained it has been pointed out that the product which is an object of the present invention is quite superior, as regards antalgic activity, than the comparison product. In fact, while after two hours from administration of Product A the rat does not tolerate the algic stimulus more than 30 seconds, on the contrary, the rat tolerates the same algic stimulus even for 45 seconds after administration of equal doses of the product which is an object of this invention (Product B).

The following examples serve to better illustrate the present invention without, however, limiting the scope thereof.

EXAMPLE 1

To a chloroforum solution (60 ml) of 7.2 g of 1-(p-chlorobenzoyl)-5-methoxy-2-methylindole-3-acetic acid and 2 g of triethylamine, 4 g of bromophthalide, previously dissolved into 20 ml chloroform, are added.

The so obtained solution is kept under stirring during about eight hours at room temperature, then the organic phase is washed with a water solution of sodium carbonate then with tap water; the organic phase is then anhydrified over sodium sulphate, and it is taken to dryness according to usual techniques.

The residue, which corresponds to 1-(p-chlorobenzoyl)-5-methoxy-2-methylindole-3-oxo-1-isobenzofuranyl ester, is crystallised from methylcellosolve. 7.3 g of the derived product are obtained.

Yield: 78.5%

Analytical data: melting point 152°-153° C.

Percent analysis
- found C 66.05% H 4.15% N 2.80%
- calc. C 66.19% H 4.11% N 2.86%

EXAMPLE 2

To a solution of 6 g bromophthalide in 50 ml dimethylformamide, 10.8 g of 1-(p-chlorobenzoyl)-5-methoxy-2-methylindole-3-acetic acid, sodium salt are added. The solution is let react, while stirring at room temperature, during about eight hours, then it is poured into 300 ml of water/ice and extracted with chloroform.

The organic phase is washed with a water solution of sodium carbonate, until required, then it is washed with water and anhydrified over sodium sulphate to dryness. The residue which corresponds to the desired product is crystallised from methylcellosolve.

9.8 g of 1-(p-chlorobenzoyl)-5-methoxy-2-methylindole-3-acet-3-oxo-1-isobenzofuranyl ester are obtained.

Yield: 70%

The analytical data corresponds to that provided at Example 1.

EXAMPLE 3

To a solution of 6 g bromophthalide in 50 ml dimethylformamide, 11.3 g of 1-(p-chlorobenzoyl)-5-methoxy-2-methylindole-3-acetic acid, potassium salt, at room temperature are added. The solution is let react, while stirring at room temperature, during about eight hours, then it is poured into 300 ml of water/ice and is extracted with chloroform. The organic phase is washed with a sodium carbonate water solution, until required, then it is washed with water and is anhydrified over sodium sulphate to dryness. The residue which corresponds to the desired product is crystallized from methylcellosolve.

10.1 g of 1-(p-chlorobenzoyl)-5-methoxy-2-methylindole-3-acet-3-oxo-1-isobenzofuranyl ester are obtained.

Yield: 72.1%

The analytical data corresponds to that provided at Example 1.

The product which is an object of the present invention appears as a crystalline powder, lightly straw-coloured, with a bitter taste.

Figure 1B:
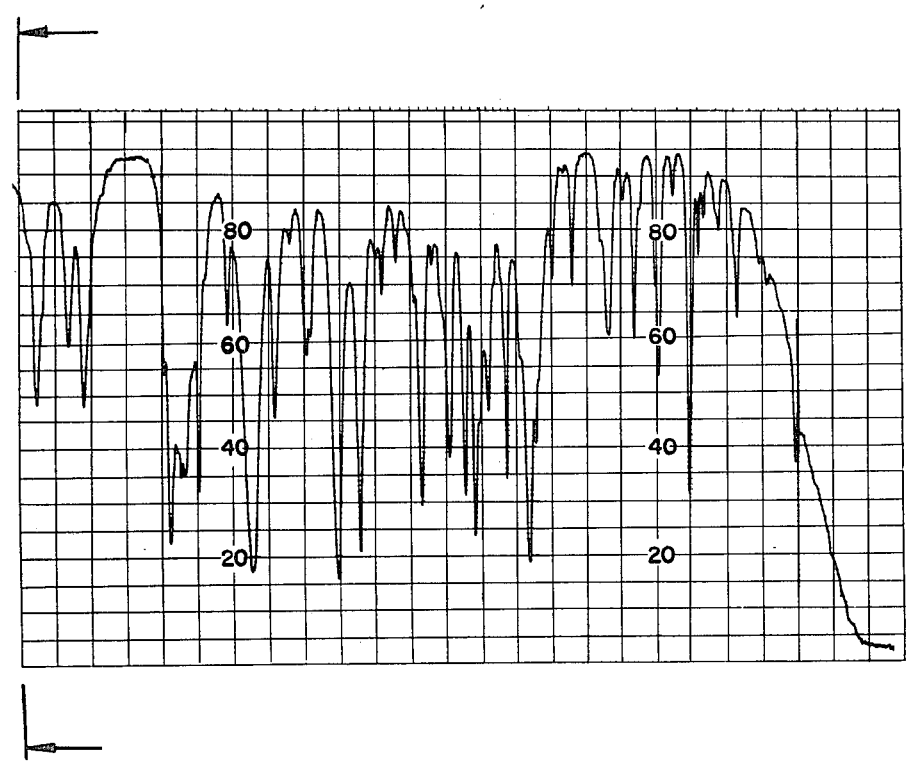

The I.R. spectrum, enclosed (FIGS. 1A and 1B). Such figures complete each other and on the abscissas inferiorly the wave number in $cm^{-1}$ and inferiorly the wave lengths in micron are indicated, and on the ordinate the percent transmittance is indicated. Moreover, as solvent nujol is used. Scan mode: 13; slit: N; time constant:auto. Such figures prove the occurred esterification as indicated by the presence of bands at 1800 $cm^{-1}$ (stretching: cyclic C=O) and 1775 $cm^{-1}$ (stretching:ester C=O).

Figure 2:
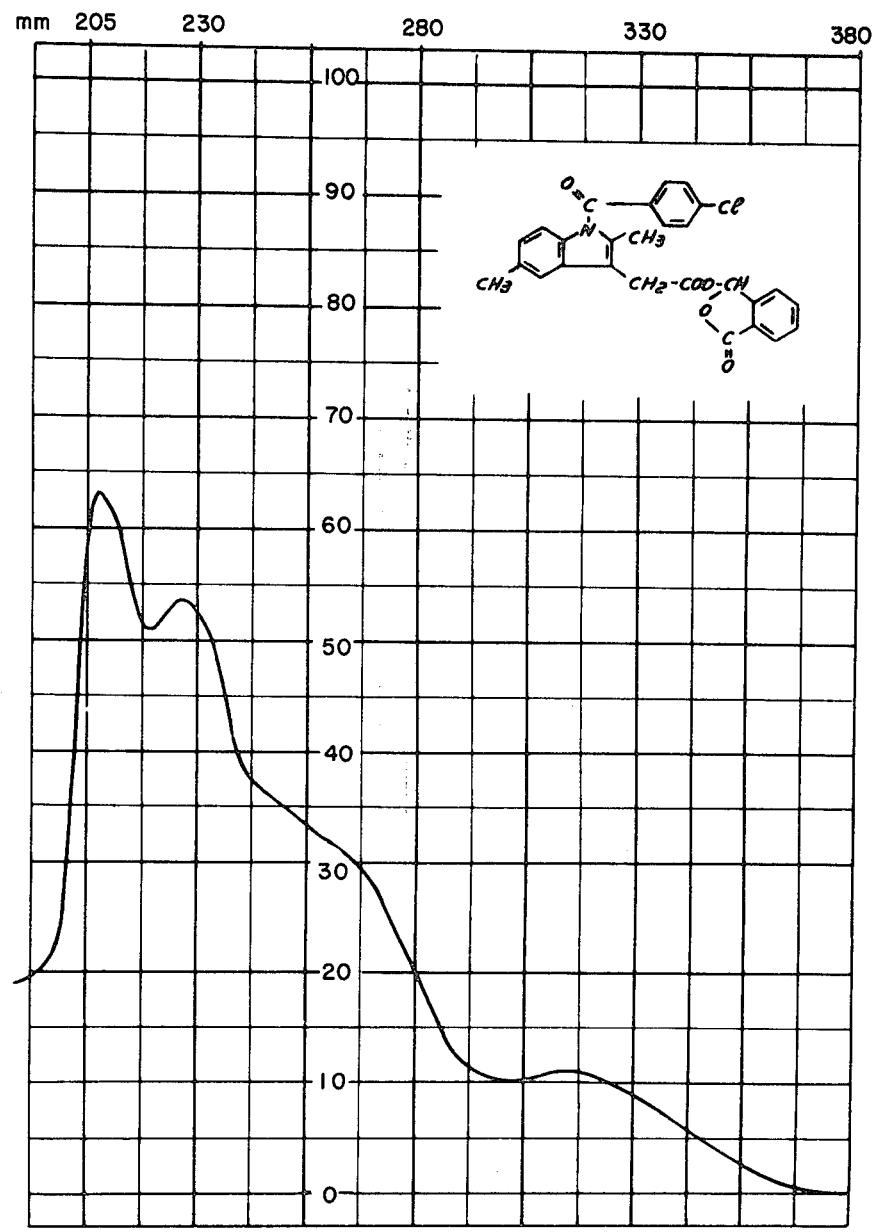

The U.V. spectrum, enclosed (FIG. 2) has the following characteristic absorption maximum when employing as a solvent ethanol at the concentration of $0.936 \times 10^{-2}$ mg/ml:

Max 317 (±2)nm $E_1^1$ 117.5

Max 227 (±2)nm $E_1^1$ 574.8

Max 207 (±2)nm $E_1^1$ 673.1

Figure 3A:
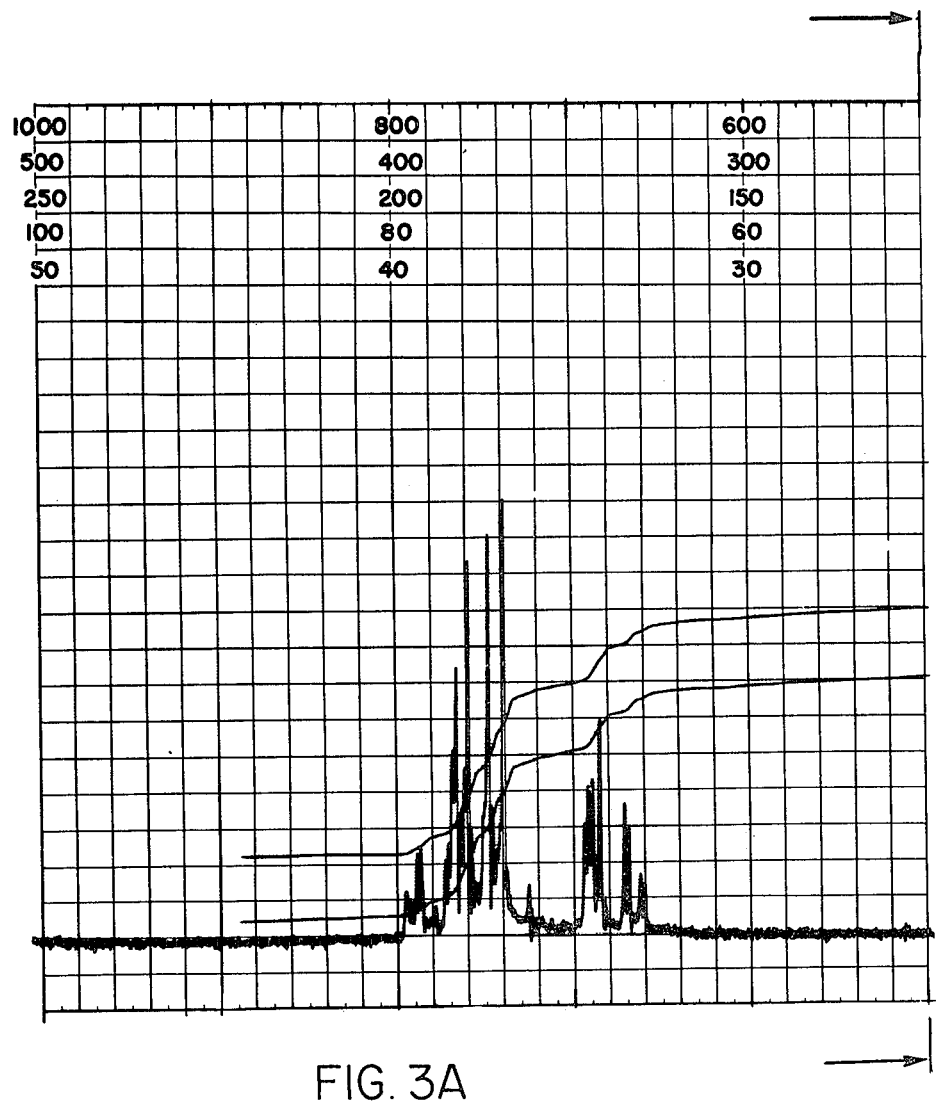
Figure 3B:
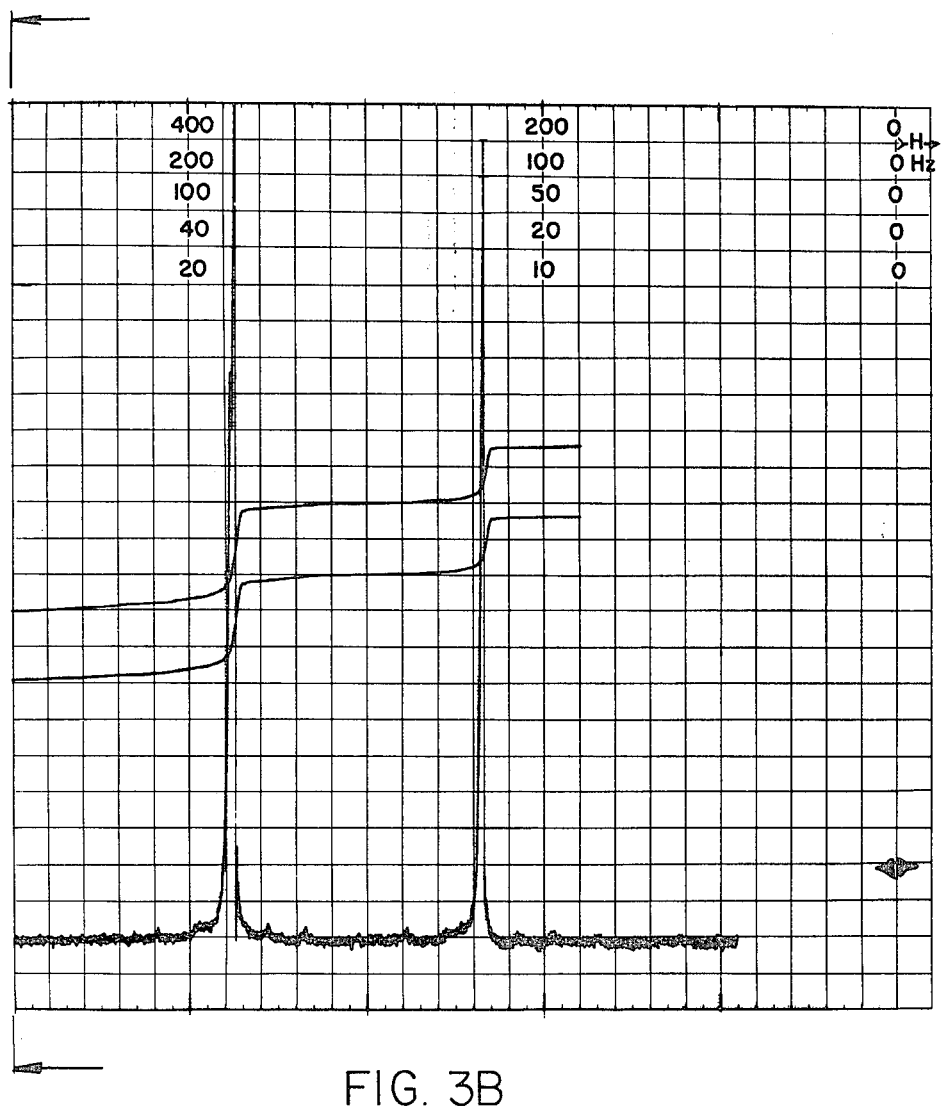

The N.M.R. spectrum, enclosed (FIGS. 3A and 3B), shows the following characteristic bands:

at $\simeq 2.35\delta$ singlet $CH_3$ at $\simeq 3.75\delta$ $OCH_3 + CH_2$ two signlets between $6.65\delta$ and 8 aromatic hydrogen plus the singlet of CH at $\simeq 6.85\delta$ of the phtlalide group.

The present invention has an object pharmaceutical compositions containing therapeutically useful amounts of the derivative which is an object of this invention, either alone or in mixture with solid or liquid or semiliquid, non-toxic and physioligically compatible, excipients. When referring to solid compositions, for oral administration, one means troches, tablets, pills, gastro-resistant troches and pills, granulates, powders to be dispersed into suitable liquid vehicles. Moreover, the active substance may be mixed, as usually done in the pharmaceutical technique, with sweetening agents, either synthetic or natural, taste-corrective, lubricating agents.

The liquid composition for oral use include emulsions, pseudosolutions, suspensions, elixirs, syrups, with a suitable liquid or semi-liquid, non-toxic and physiologically compatible, carrier.

Further, in said liquid and semi-liquid compositions, there may be included moistening or suspending substances, sweetening agents, taste-correctives, aromatizing agents. The compositions, for rectal use contain, beside the active substance, fatty substances of animal and vegetable origin, synthetic natural, semi-synthetic oils, lubricant agents and all that is normally used in the art.

The product of active substance contained in each pharmaceutical formulation may vary in ratio between the single dose and the therapeutical dose/die.

The following examples of pharmaceutical formulations are provided only for explicative scope and are not limiting.

EXAMPLE 4

Each 50 mg capsule contains:

| | |
|---|---|
| Each 50mg capsule contains: | |
| 1-(p-chlorobenzoyl)-5-methoxy-2-methylindole-3-acet-3-oxo-1-isobenzofuranyl ester | 25 mg |
| talc | 15 mg |

EXAMPLE 5

Each 100 mg capsule contains:

| | |
|---|---|
| 1-(p-chlorobenzoyl)-5-methoxy-2-methylindole-3-acet-3-oxo-1-isobenzofuranyl ester | 50mg |
| Mais starch | 30mg |

EXAMPLE 6

Each suppository of 50 mg or 100 mg of active substance contains, 2 g and 2.2 g, respectively, of a mixture of semi-synthetic unsaturated fats and cocoa-butter.

I claim:

1. 1-(p-Chlorobenzoyl)-5-methoxy-2-methyl indole-3-acetic acid-3-oxo-1-isobenzofuranyl ester.

2. An analgesic and anti-infammatory composition, which comprises an analgetic or anti-inflammatory amount of the compound according to claim 1 and a pharmaceutical carrier.

3. Pharmaceutical compositions in dosage unit form comprising from about 25 mg to about 100 mg of the compound according to claim 1 in a mixture with a pharmaceutical carrier.

* * * * *